(12) United States Patent
Plank et al.

(10) Patent No.: US 6,969,254 B2
(45) Date of Patent: Nov. 29, 2005

(54) DENTAL APPARATUS

(75) Inventors: Wolfgang Plank, Rankweil (AT); Thomas Stahl, Bregenz (AT)

(73) Assignee: Ivoclar Vivadent AG., Schaan (LI)

( * ) Notice: Subject to any disclaimer, the term of this patent is extended or adjusted under 35 U.S.C. 154(b) by 286 days.

(21) Appl. No.: 10/242,918

(22) Filed: Sep. 12, 2002

(65) Prior Publication Data

US 2003/0113685 A1    Jun. 19, 2003

Related U.S. Application Data

(60) Provisional application No. 60/354,534, filed on Feb. 5, 2002.

(30) Foreign Application Priority Data

Dec. 18, 2001  (DE) ................................. 101 62 231

(51) Int. Cl.⁷ ............................. A61C 3/00; A61C 1/02
(52) U.S. Cl. ........................... 433/29; 433/98; 433/101
(58) Field of Search .............................. 433/29, 98, 99, 433/101; 250/504 H

(56) References Cited

U.S. PATENT DOCUMENTS

| | | | | |
|---|---|---|---|---|
| 4,208,579 A | * | 6/1980 | Scrivo et al. .......... 250/227.22 |
| 5,634,711 A | * | 6/1997 | Kennedy et al. ............. 362/119 |
| 5,880,826 A | * | 3/1999 | Jung et al. ..................... 356/73 |
| 5,912,470 A | * | 6/1999 | Eibofner et al. ........ 250/504 H |
| 5,922,605 A | * | 7/1999 | Feurstein et al. ............. 436/55 |
| 5,975,895 A | | 11/1999 | Sullivan |
| 6,506,050 B1 | | 1/2003 | Steddin ....................... 433/98 |
| 6,571,049 B1 | * | 5/2003 | Nath .......................... 385/139 |
| 6,655,946 B2 | * | 12/2003 | Foreman et al. ............ 425/145 |
| 2001/0023056 A1 | * | 9/2001 | Grunenfelder et al. ........ 433/27 |

FOREIGN PATENT DOCUMENTS

| | | |
|---|---|---|
| DE | 196 18 542 A1 | 5/1996 |
| DE | 198 46 580 A1 | 4/2000 |
| DE | 199 43 393 C1 | 1/2001 |
| DE | 199 48 620 A1 | 4/2001 |
| DE | 101 04 579 A1 | 9/2002 |
| WO | WO 01/60280 | 8/2001 |

* cited by examiner

Primary Examiner—John J Wilson
(74) Attorney, Agent, or Firm—John C. Thompson; Alan S. Korman

(57) ABSTRACT

A dental apparatus for hardening dental restoration components is provided that includes a control device controllable via a wireless communications unit and operable to exchange data with a communications unit. The control device is programmable to configure the control device to control a polymerization cycle and is connected with the communications unit with which the control unit exchanges data for changing the programming of the control device.

13 Claims, 1 Drawing Sheet

DENTAL APPARATUS

CROSS-REFERENCE TO RELATED APPLICATIONS

This application claims foreign priority benefits under 35 U.S.C. §119(a)-(d) from German patent application ser. no. P 101 62 231.7 filed Dec. 18, 2001. In addition, this application claims the benefit under 35 U.S.C. §119(e) of U.S. provisional patent application Ser. No. 60/354,534 filed Feb. 5, 2002.

BACKGROUND OF THE INVENTION

The present invention relates to a dental apparatus.

In connection with the concept of a dental apparatus for hardening dental restoration pieces, the concept comprises dental light hardening apparatus, other polymerization apparatus, and dental ovens as well, whereby the concept "hardening" also encompasses ceramic combustion. In the following description, the present invention is described in connection with a light hardening device.

A dental apparatus of this type—namely, a light hardening device—has been disclosed in U.S. Pat. No. 6,695,614. In accordance with this patent a light hardening device is configured for effecting the hardening of dental material comprised of light- or heat-polymerizable plastic, whereby the frequency and the emissions spectrum of the emitted light radiation, as well as the length of irradiation and the intensity, are accommodated to the requirements therefor across a wide range.

To make available an improved dental restoration result, new polymerizable masses are continually being developed. A result which appropriately exploits these developments can only be successful, however, if the polymerization cycle—that is, the parameter concerning the performance of the polymerization process until its completion—is accommodated to the material which is used.

If a manufacturer develops a new material, appropriate accommodations to the existing, non-programmable light hardening devices must be undertaken, via efforts on the manufacturer's part, in order to optimally program for the new material. In the aforementioned patent, a light hardening device is proposed which, in view of the parameters of the polymerization cycle, is programmable which, to this extent, represents an improvement.

Additionally, in U.S. Pat. No. 5,922,605, a programmable device for controlling a light hardening device is disclosed. This programming device permits the control of the time periods for the actuation of a light source and a heat source, whereby it is to be understood that the time-based control of the polymerization process is dependent upon the type of workpiece to be polymerized.

OBJECTS AND SUMMARY OF THE INVENTION

In contrast, the present invention provides a solution to the challenge of providing a dental apparatus which can be flexibly deployed in hand-held applications and which can accommodate future developments without putting the security of the polymerization operation at risk.

The dental apparatus of the present invention also permits the control apparatus to be remotely accommodated or adjusted to new material. Additionally, the program parameters can, for example, be changed, if it has been established in hindsight that, for example, a longer or shorter hardening period in a certain program segment would be more favorable or if the given light radiation intensity during a different irradiation application leads to a more advantageous hardening result. Thus, programs can be newly installed or changed if one wants to undertake a calibration of the device and conduct diagnostic, maintenance, or quality assurance work. Moreover, the dental apparatus can also be operated in a cable-free manner via an accumulator or battery.

In accordance with the present invention, a communications unit is preferably provided which is coupled with a control device and via which the programming of the control device can be changed. The communications unit can be configured in any suitable, desired manner. A wireless telephone operating in accordance with the GSM standard and having an infrared interface can serve, for example, as the communications device. In this manner, a remote programming of the dental apparatus can be accomplished in a simple manner. In connection with this solution, it is no longer required that the dentist must, for example, personally operate the personal computer to effect a programming change, whereby service or programming mistakes are to this extent largely foreclosed.

It is to be understood that a communication via radio transmissions or ultrasound transmission is also possible in connection with, for example, a personal computer having a corresponding configuration for wireless data transmission. The communications unit of the present invention includes, at the least, a receiving capability so that data from the programmable control device can be relayed thereto and, preferably, also includes a transmission capability so that a bi-directional communication is possible. In connection with the bi-directional configuration of the communications unit, an automatic remote calibration can also be realized. If the light hardening device comprises, for example, a glow lamp such as a halogen glow lamp, which serves as the light source, a regularly scheduled exchange of this component is required. Glow lamps correspond to one another only broadly in connection with their light intensity and their light radiation or emission spectrum. A remote calibration is possible, for example, in that the light emitted by a newly installed halogen glow lamp can be conducted to a suitable light sensor which is in communication with the communications unit. Via a remote calibration, a warning signal can be given, for example, if the exchanged halogen glow lamp does not correspond to the operational requirement profile.

It is to be understood that the communication device can be configured in any suitable, desired manner. If a semiconductor light emitting source is used, suitable infrared sending diodes and photodiodes sensitive in the infrared range can be provided with LED chips on a common base body, whereby the production of the device is simplified.

If the light guide rod includes a so-called anti-aliasing or cut-off filter—that is, a filter which holds back the heat radiation—it is possible to dispose the infrared diodes adjacent to a red window.

On the other hand, it is to be understood that the radio transmission also is effected by a communications unit which is disposed in the grip portion of a hand grip component.

Further advantages, details, and features are described hereinafter in connection with a description of one embodiment of the present invention with reference to the figures of the drawings, in which a preferred embodiment of this invention is illustrated.

DETAILED DESCRIPTION

Figure 1:
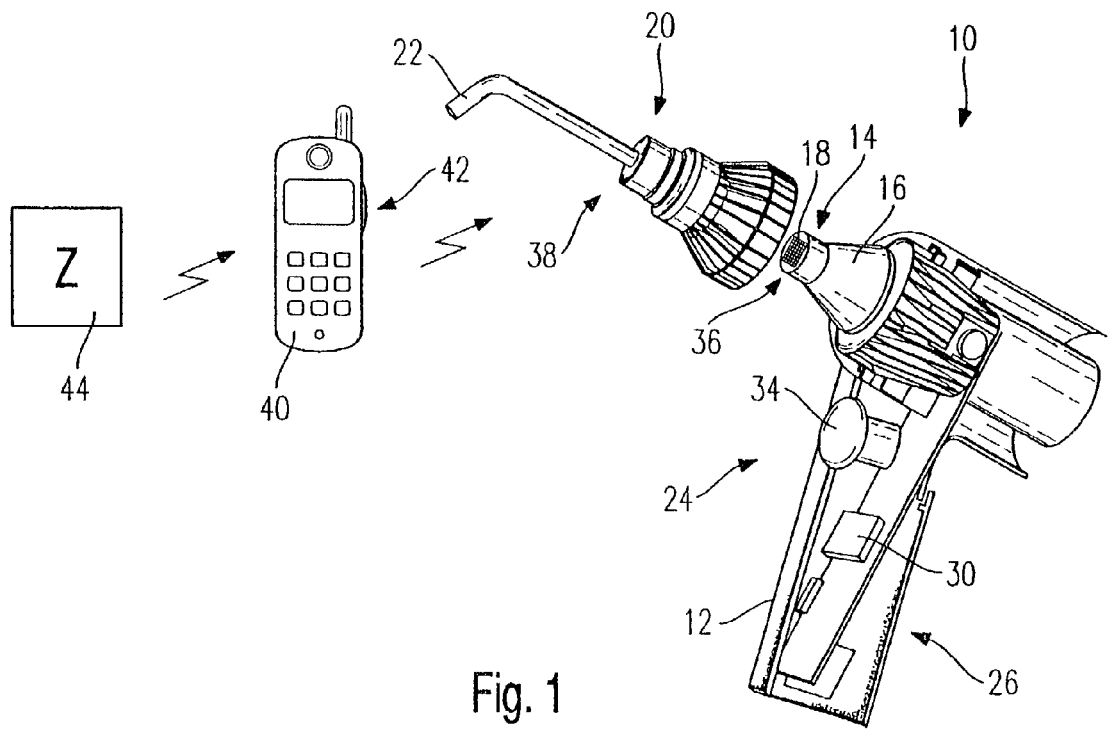
FIG. 1 is a schematic view of one embodiment of the light hardening device of the present invention adapted for operation in a remote programming mode.

FIG. 1 shows a schematic view of a light hardening device 10 of the present invention. The light hardening device includes, in a conventional manner, a housing 12, which, for the purpose of clarity, is shown in FIG. 1 with a half portion thereof omitted. The housing 12 includes the proven pistol shape. A light source 14 is configured as a semi-conductor light emitting source with a plurality of LED chips 18 mounted on a common base body 16. A front portion 20 of the light hardening device 10 has been removed in the view of the device shown in FIG. 1 in order to make available a view of the light source 14. It is to be understood that this portion is, in practice, firmly secured with the remaining portion of the light hardening device 10.

The front portion 20 secures the mounting on the light hardening device 10 of suitable optical apparatus such as a focusing apparatus which conduct the light emitted by the light source 14 to a light guide rod 22.

The light hardening device 10 includes a grip component 24 in which a base station is comprised, which is not shown in FIG. 1. In a first embodiment of the present invention, the grip component 24 is provided with a plurality of accumulators in the hand grip portion 26 thereof and the base station serves to charge or load the accumulators upon insertion of the grip portion component 26 in a suitably configured stand.

In a second embodiment of the present invention, a power supply cable extends between the base station and the grip component through which flows the electrical energy for the operation of the hand piece.

The hand grip portion 26 further includes a control device 30, which is schematically shown in FIG. 1. The control device 30 is programmable and ensures that, upon the application of pressure to an actuation button 34, a program is begun which controls the intensity and the length of application of the light emitted by the LED chips 18 in a suitable manner. The LED chips can also, for example, be combined with differing spectral emissions maxima, which are actuatable in common as a group and can be individually controlled by the control device 30.

In the illustrated embodiment of a light hardening device 10, the base body 16 also supports a communications unit 36. In this connection, two diodes—namely, an infrared transmitting diode and an infrared receiving diode—are disposed adjacent the LED chips 18 on the base body 16. In front of both of these diodes, the front portion 20 supports a red window 38 which, in the illustrated embodiment, is disposed closely adjacent the entrance or beginning of the light guide rod 22. The transmission performance of the infrared diode is sufficient for data transmission over several meters. In a similar manner—that is, in any event, with an infrared sending or transmitting diode and an infrared receiving diode—a wireless telephone 40 with such components and operable in accordance with the GSM standard or the UMTS standard, is in a position to communicate with the grip portion 24 of the light hardening device 10 via its communications unit 36. The infrared interface 42 of the wireless telephone is preferably oriented toward the light hardening device 10 in a manner similar to, for example, the manner in which a remote control is oriented toward a television for remote infrared control of the television.

A connection is created by a signal transmission with a central programming control unit 44 which is provided from the manufacturer and which permits bi-directional data communication between the manufacturer and the light hardening device for effecting programming of the control device 30.

Figure 2:
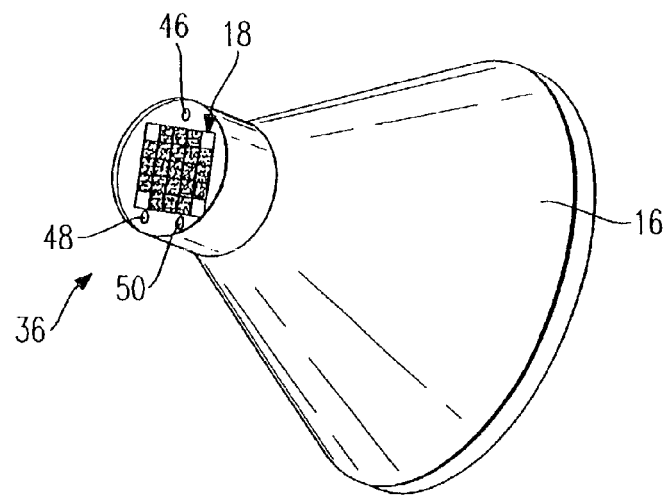
FIG. 2 is an enlarged view of a base body for a light hardening device of the present invention.

The base body 16 can be seen in an enlarged manner in FIG. 2. In addition to the LED chips 18, a temperature sensor 46 is mounted on the base body 16. Additionally, the base body 16 includes an infrared transmitting diode 48 and an infrared receiving diode 50 disposed in opposed relation to the temperature sensor 46 and in neighboring relation to one another, the diodes together forming the communications unit 36. The base body 16 is configured as a cooling body so that the lost or process heat of the infrared transmitting diode 48 can also be guided away. Preferably, the data transmission is effected in a coded and pulsed manner in order to reduce the susceptibility to disturbances. Furthermore, it is preferred that a known data transmission standard is used so that a standard infrared interface of a wireless telephone can be used. The programming follows, in any event, preferably via a special coding and via the use of at least one checked sum in order to secure against a false programming result.

The illustrated embodiment comprises a semi-conductor light emitting source as the light source 14. In a typical conventional manner, such a light emitting source has a relatively small heat emitting portion so that the cooling requirements are still further reduced. In connection with such an approach, the shielding of the heat emitted via filters is basically not required. This permits the solution also to effect the data communication directly via the light guide rod so that it is also possible to omit the red window 38 and to orient the front end of the light guide rod 22 toward the infrared interface 42 of the telephone 40 in order to permit a data transmission therethrough.

In accordance with an especially favorable configuration, it is provided that the infrared transmitting diodes and the infrared receiving diodes 48 and 50, respectively, are disposed directly in the channels between the cooling ribs. This permits a particularly simple mounting without the need to disturb the air flow through the cooling ribs and thereby substantially negatively impact the cooling effect provided thereby.

The configuration of the light hardening device with the red window 38 is, however, preferred if a halogen glow lamp is deployed as the light emitting source, as such a light emitting source includes a comparatively higher heat emitting portion so that, frequently, an anti-aliasing filter must be deployed. The configuration with the red window has, at the same time, the advantage that false light is held back or blocked in an improved manner and the communications unit no longer requires an exact orientation between the light hardening device and the telephone.

The present invention is, of course, in no way restricted to the specific disclosure of the specification and drawings, but also encompasses any modifications within the scope of the appended claims.

What is claimed is:

1. A dental apparatus for hardening dental restoration components, comprising:
 a first bi-directional wireless communications unit; and
 a hand-held apparatus including
  a second bi-directional wireless communications unit,
  a plurality of a selected one of LEDS and laser diodes, which are arranged in substantially neighboring relationship to one another and which emit light in a manner controlled to effect the performance of a polymerization cycle, and control means for controlling the intensity and the length of application of the light emitted by the selected one of LED and laser diodes for hardening dental restoration compounds in a suitable manner, the control means being controllable via the second bi-directional wireless communications unit and operable to exchange data with the first bi-directional wireless communications unit.

2. The dental apparatus according to claim 1, wherein the control means is programmable to configure the control means to control a polymerization cycle and is connected with the second bi-directional wireless communications unit with which the control means exchanges data for changing the programming of the control means.

3. The dental apparatus according to claim 1, wherein the control means can be calibrated by transmitting thereto, via the first and second bi-directional wireless communications units, programming data for effecting calibration of the control means.

4. The dental apparatus according to claim 1, wherein the dental apparatus has a capability for wireless communication via the communications units with a programming control device which is configured as a data station or as a telephone operable in accordance with the GSM standard or the UMTS standard, the programming control device providing programming data for the control means.

5. The dental apparatus according to claim 1, wherein the communications units includes a standardized data transmission technology and is configured to establish a transmission link in accordance with the Blue Tooth standard, the wireless LAN standard, or the DECT standard.

6. The dental apparatus according to claim 1, wherein the dental apparatus includes a selected one of an infrared interface, a radio wave transmission interface, and an ultrasonic interface, which is in communication with the communications units.

7. The dental apparatus according to claim 1, wherein the communications units includes at least one infrared diode.

8. The dental apparatus according to claim 1, wherein an infrared diode is provided to serve as a receiving device in a grip component of the dental apparatus.

9. The dental apparatus according to claim 1, whereby an infrared light emitting diode is configured as a transmitting device in a grip component.

10. The dental apparatus according to claim 1, wherein at least one infrared diode is arranged in neighboring relationship to the selected ones of the LEDS and laser diodes of a grip component, and the transmission of data is effected via a light guide rod which otherwise serves to guide light emitted by the dental apparatus toward the workpiece to be irradiated.

11. The dental apparatus according to claim 1, wherein the control means is programmable outside of the polymerization cycle.

12. The dental apparatus according to claim 1, wherein an infrared transmitting diode and an infrared receiving diode are commonly mounted on a base body in neighboring relationship to the selected ones of the LEDS and the laser diodes, whereby the infrared diodes are secured by adhesion thereto.

13. The dental apparatus according to claim 1, wherein infrared diodes are in neighboring relationship to the selected ones of the LEDS and laser diodes and arranged in neighboring relationship to a separate light entrance opening in the housing of the grip component of the dental apparatus.

* * * * *